(12) United States Patent
Astle (10) Patent No.: US 9,575,084 B1
(45) Date of Patent: Feb. 21, 2017

(54) DRIED SPECIMEN STORAGE SLIDE

(75) Inventor: Thomas W. Astle, Orange, CT (US)

(73) Assignee: Thomas W. Astle, Orange, CT (US)

( * ) Notice: Subject to any disclaimer, the term of this patent is extended or adjusted under 35 U.S.C. 154(b) by 1269 days.

(21) Appl. No.: 12/868,229

(22) Filed: Aug. 25, 2010

(51) Int. Cl.
*G01N 21/75* (2006.01)
*G01N 35/00* (2006.01)
*B01L 3/00* (2006.01)
*G01N 33/49* (2006.01)

(52) U.S. Cl.
CPC .......... *G01N 35/0098* (2013.01); *B01L 3/502* (2013.01); *B01L 3/5021* (2013.01); *G01N 33/491* (2013.01)

(58) Field of Classification Search
CPC .. G01N 31/22; G01N 33/525; G01N 35/0098; G01N 33/491; B01L 2400/0406; B01L 3/502; B01L 3/5021
See application file for complete search history.

(56) References Cited

U.S. PATENT DOCUMENTS

| | | | | |
|---|---|---|---|---|
| 4,668,472 | A * | 5/1987 | Sakamoto et al. | 422/401 |
| 4,948,442 | A * | 8/1990 | Manns | 156/73.1 |
| 5,139,031 | A * | 8/1992 | Guirguis | 600/584 |
| 5,139,685 | A * | 8/1992 | de Castro et al. | 210/767 |
| 5,597,532 | A * | 1/1997 | Connolly | 422/401 |
| 5,665,238 | A * | 9/1997 | Whitson et al. | 210/649 |
| 6,129,214 | A | 10/2000 | Bar-Ami et al. | |
| 6,818,180 | B2 * | 11/2004 | Douglas et al. | 422/417 |
| 7,838,509 | B2 | 11/2010 | Ellington et al. | |
| 8,025,850 | B2 * | 9/2011 | Chan | 422/401 |
| 2007/0202542 | A1 * | 8/2007 | Babu et al. | 435/7.1 |

FOREIGN PATENT DOCUMENTS

| | | |
|---|---|---|
| EP | 1056336 | 3/2005 |
| WO | 0112783 | 2/2001 |

OTHER PUBLICATIONS

Efficiency of Hyaluronic Acid (HA) Sperm Selection; Parmegiani et al.; Journal of Assisted Reproduction and Genetics; vol. 27, pp. 13-16, Dec. 30, 2009.
Efficacy of Hyaluronic Acid Binding Assay in Selecting Motile Spermatozoa With Normal Morphology at High Magnification; Peterson et al., Reproductive Biology and Endocrinology; vol. 8:149, pp. 1-7, Dec. 3, 2010.

* cited by examiner

*Primary Examiner* — Krishnan S Menon
*Assistant Examiner* — Dwan A Gerido
(74) *Attorney, Agent, or Firm* — DeLio, Peterson & Curcio, LLC; Kelly M. Nowak (57) ABSTRACT

Specimen collection slides, methods of fabricating and methods of utilizing such specimen collection slides whereby each specimen collection slide includes a top rigid layer with an opening, a bottom rigid layer with an opening substantially the same size as the top layer opening, a middle rigid section having an opening larger than the openings in both the top and bottom layers, and a filtration media residing within the opening in the middle section. The top, bottom and middle are secured together to provide the resultant slide with thickness and rigidity that lends the slide to be utilized in automated handling processes and instruments. The middle section of the slide encases the filtration media and sandwiches it between the top and bottom layers so that the filtration media is protected from damage. Each slide may have its own unique identifier.

25 Claims, 7 Drawing Sheets

DRIED SPECIMEN STORAGE SLIDE

BACKGROUND OF THE INVENTION

1. Field of the Invention

The present invention is directed to specimen storage, and in particular, to methods of use and specimen storage slides for the transportation and storage of dried specimens.

2. Description of Related Art

A variety of fields implement the use of cards to store dried specimens. These specimens may include chemical samples, biological samples, and the like. For instance, dried blood spots stored on paper cards have been in use for years in a variety of fields ranging from clinical, preclinical, research, forensics, and the like. More recently there has been an increase in the use of dried blood spots in clinical applications, such as, in neo-natal screening, DNA analysis, disease analyses (infectious disease, blood glucose concentration, etc.), drug screenings, and the like. Preclinical applications for dried blood spots, such as, medical research, drug discoveries, and the like, are also becoming more prevalent.

In the collection of dried blood spots, a number of drops of obtained blood are deposited in predetermined locations on filter paper of a paper collection card. These collection cards include an absorbent filter paper that is encased within a cardboard frame, attached inside a cardboard card, or attached to a paper sheet. The collection cards may also be provided with a source for sample identification, such as, a demographic portion where information about the sample and the submitter's identification can be entered. The blood specimen is allowed to dry on the collection card for storage, transportation and/or later use thereof.

However, a detriment of the currently available specimen collection cards is that since they are composed of either paper sheets or cardboard these conventional collection cards are flimsy and easily damaged. Also, in collection cards having a paper or cardboard frame encasing the filter paper media, the frame is typically not much thicker than the filter paper media it encases. As such, when one or more of these types of cards are stacked upon one another, their respective filter paper medias contact each other causing sample cross contamination, which is highly undesirable. Accordingly, it is often necessary to store each framed paper or cardboard collection card in an envelope separate from one another.

Furthermore, both current and future clinical and preclinical application systems or equipment are leaning towards automated handling, automated processing, and/or automated sample collection. Currently available paper and/or cardboard collection cards are inadequate for automated handling, processing, and/or sample collection due to their flimsiness or lack of dimensional stability. Rather, these conventional cards must be individually hand picked and placed into or onto the automated systems and equipment to prevent damage thereto, which in turn, leads to slower processing times and more costly analyses.

Accordingly, a need exists in the art for improved specimen collection storage devices that are durable, easily useable, are structurally and mechanically stable, have sufficiently rigidity for handling and processing, avoid specimen cross contamination, are adapted for automated handling, automated processing, and/or automated sample collection, and allow for faster processing times and reduced costs.

SUMMARY OF THE INVENTION

Bearing in mind the problems and deficiencies of the prior art, it is therefore an object of the present invention to provide specimen collection slides that are durable and both structurally and mechanically stable.

It is another object of the present invention to provide specimen collection slides having sufficient rigidity for manual and/or mechanically automated handling and processing.

A further object of the invention is to provide specimen collection slides that prevent cross contamination of specimens residing on adjacent slides.

Another object of the present invention is to provide specimen collection slides that are easily useable, cost effective and allow for faster processing times.

It is yet another object of the present invention to provide methods of making and implementing the various specimen collection slides in accordance with the various embodiments of the invention.

Still other objects and advantages of the invention will in part be obvious and will in part be apparent from the specification.

The above and other objects, which will be apparent to those skilled in the art, are achieved in the present invention which is directed to a specimen collection slide that includes a first layer of a first non-fibrous material having a first central opening; a second layer of a second non-fibrous material having a second central opening attached to the first layer, the first and second central openings being in alignment with each other; and a filtration media layer for retaining a sample residing between the first and second layers, the filtration media being accessible through both the first and second central openings whereby together the first and second layers provide the specimen collection slide with a thickness sufficient for handling.

The specimen collection card may be a first specimen collection slide in contact with a second specimen collection slide, whereby one of the first or second layers of the first specimen collection slide contacts an outer non-fibrous layer of the second specimen collection slide to provide a distance between adjacent filtration media layers of the first and second specimen collection slides, the distance preventing contact between the adjacent filtration media layers and preventing cross-contamination of any samples residing on the adjacent filtration media layers.

The second layer of the specimen collection card may have a recessed ledge within and extending around the perimeter inside the second central opening, the recessed ledge receiving and holding the filtration media within the specimen collection slide in a manner that avoids any damage to the filtration media.

The specimen collection card may further include the filtration media layer having an internal standard. The first and second layers of the specimen collection card may be an identical material, and have substantially identical external dimensions and thickness. The non-fibrous material of the first and second layers may be a plastic material. The first and second layers may be bonded or welded together, and the thickness of the specimen collection slide is sufficient for automated handling.

The specimen collection card may further include an identifier on the first layer that uniquely identifies the specimen collection slide. The filtration media layer of the specimen collection slide may contain one or more dried samples selected from the group consisting of biological samples, chemical samples, or combinations thereof.

In other embodiments the invention is directed to a specimen collection slide that includes a first rigid layer having a first central opening; a second rigid layer having a second central opening larger than the first central opening;

a filtration media layer for retaining a sample residing entirely within the second central opening of the second rigid layer, the second rigid layer protecting the filtration media from damage thereto; and a third rigid layer having a third central opening substantially the same size as the first central opening. The first, second and third rigid layers have substantially identical external dimensions, and are securely attached together without damaging the filtration media to provide the specimen collection slide with a thickness sufficient for handling.

The thickness of the specimen collection slide is sufficient for automatic handling of the specimen collection slide. The specimen collection card may further include the filtration media layer having an internal standard. The first, second and third rigid layers may be an identical material, and have substantially identical external dimensions. The first, second and third rigid layers may be a plastic material, whereby the plastic material may be a thermoplastic polymer. The first, second and third rigid layers may be bonded together or ultrasonically welded together.

The specimen collection card may further include a unique identifier on each specimen collection slide for distinguishing one specimen collection slide from another. When the specimen collection slide is a first specimen collection slide in contact with a second specimen collection slide, one of the plastic layers of the first specimen collection slide contacts one of the plastic layers of the second specimen collection slide to provide a distance between adjacent filtration media layers of the first and second specimen collection slides. This distance prevents contact between the adjacent filtration media layers and prevents cross-contamination of any samples residing on the adjacent filtration media layers.

The filtration media layer of the specimen collection slide may contain one or more dried samples selected from the group consisting of biological samples, chemical samples, or combinations thereof. The filtration media layer may have one or more delineated locations that identify one or more samples. The one or more samples on the filtration media layer may be from a same source. The one or more delineated locations may uniquely identify and distinguish the one or more samples on the same specimen collection slide from one another. The one or more samples on the filtration media layer may be from different sources.

In still other embodiments the invention is directed to one or more methods of fabricating a specimen collection slide that includes providing a first rigid layer having a first central opening; providing a second rigid layer having a second central opening larger than the first central opening; positioning a filtration media layer entirely within the second central opening of the second rigid layer to protect the filtration media; providing a third rigid layer having a third central opening substantially the same size as the first central opening; aligning the first, second and third rigid layers so that the second rigid layer and the filtration media layer reside between the first and third rigid layers; and securing the first, second and third rigid layers together without damaging the filtration media.

In these embodiments, the specimen collection slide may have a total thickness sufficient for automatic handling. The methods may further include pre-treating the filtration media layer with an internal standard. The first, second and third rigid layers may comprise an identical material. The first, second and third rigid layers may comprise a plastic material. The first, second and third rigid layers may be bonded or ultrasonically welded together.

The methods may further include providing a unique identifier on an outer surface of the specimen collection slide. The methods may further include providing one or more delineated markings on the filtration media layer for identifying locations of one or more samples. The methods may include the one or more delineated markings uniquely identify and distinguish the one or more samples from one another on the same specimen collection slide.

In these methods the specimen collection slide may be a first specimen collection slide, and the methods further includes providing a second of the specimen collection slide, whereby the first and third rigid layers of the first specimen collection slide each has a thickness such that when the first specimen collection slide is provided adjacent the second specimen collection slide, a combined thickness of the first or third rigid layer of the first specimen collection slide and an outer rigid layer of the second specimen collection slide together provide a distance between adjacent filtration media layers of the first and second specimen collection slides, the distance preventing contact between the adjacent filtration media layers and preventing cross-contamination of any samples residing on the adjacent filtration media layers.

The methods may further include storing a plurality of specimen collection slides adjacent one another within a cassette holder. The cassette holder may be provided with a unique identifier linked to the specimen collection slides stored therein. The cassette holder may further include a desiccant therein.

In further embodiments the invention is directed to one or more methods of utilizing a specimen collection slide that includes providing a specimen collection slide that includes a top rigid layer with a first central opening, a bottom rigid layer having a second central opening substantially the same size as the first central opening, a middle rigid layer having a third central opening larger than both the first and second central openings, a filtration media layer residing entirely within the central opening of the middle rigid layer, both the filtration media and the middle rigid layer residing between the top and bottom rigid layers, whereby the top, middle and bottom rigid layers are securely attached together. The methods proceed with obtaining at least one specimen from at least one source; accessing the filtration media layer through one of the first or second central openings; depositing the at least one specimen onto the filtration media; absorbing the at least one specimen into the filtration media; and allowing the deposited at least one specimen to dry on the filtration media for a subsequent analytical testing procedure.

The specimen collection slide has a total thickness sufficient for automatic handling. The filtration media layer may include an internal standard. The top, middle and bottom rigid layers may be an identical material. The top, middle and bottom rigid layers may be a plastic material. The top, middle and bottom rigid layers may be bonded or ultrasonically welded together. The top or bottom rigid layer may have an identifier that uniquely identifies the specimen collection slide. The at least one specimen may be deposited onto one or more delineated locations on the filtration media layer.

The one or more delineated locations may each include its own unique identifier on the filtration media layer for distinguishing the one or more delineated locations from each other. The at least one specimen may be a biological sample, a chemical sample or a combination thereof. The at least one specimen may be a blood sample, such that, the at least one dried specimen comprises a dried blood spot.

The methods may further include obtaining and depositing a plurality of specimens from a single source. The methods may further include obtaining and depositing a plurality of specimens from different sources.

When the specimen collection slide is a first specimen collection slide having a first filtration media layer with one or more dried specimens thereon, the methods may further include providing a second specimen collection slide having a second filtration media layer with one or more other dried specimens thereon; and providing the second specimen collection slide over the first specimen collection slide such that the top rigid layer of the first specimen collection slide contacts the bottom rigid layer of the second specimen collection slide, whereby a thickness of the top rigid layer of the first specimen collection slide and a thickness of the bottom rigid layer of the second specimen collection slide together provide a distance between the first filtration media layer and the second filtration media layer that prevents contact between the adjacent filtration media layers and prevents cross-contamination of any samples residing on the adjacent filtration media layers.

The methods may further include storing a plurality of specimen collection slides adjacent one another within a cassette holder. The cassette holder may be provided with a unique identifier linked to the specimen collection slides stored therein. The methods may further include providing a desiccant within the cassette holder.

The methods may further include performing the analytical testing procedure using the specimen collection slide having the at least one dried specimen on the filtration media. The analytical testing procedure may be one or more procedures selected from clinical applications, preclinical applications, experimental testing applications, field-test applications and combinations thereof.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

In describing the preferred embodiment of the present invention, reference will be made herein to FIGS. 1A-6B of the drawings in which like numerals refer to like features of the invention. Terms such as "upper", "lower", "inner", "outer", "inwardly", "outwardly", "vertical", "horizontal", and the like, when used herein, refer to the positions of the respective elements shown in the accompanying figures and the present invention is not limited to such positions.

The present invention is directed to specimen collection slides and methods of use thereof. The various specimen collection slides of the invention are durable, structurally and mechanically stable, and have sufficient rigidity for handling and processing in automated systems and/or equipment. With the increasing use of specimen collection slides in both preclinical and clinical applications, the one or more embodiments of the invention allow for easy and efficient automated handling, automated processing, and/or automated sample collection using the specimen collection slides of the invention. The configurations of the present specimen collection slides also prevent cross contamination of specimens residing on adjacent collection slides both during the use and storage of such slides.

In accordance with the various embodiments, the specimen collection slides of the invention may be used in both preclinical applications and clinical applications. Preclinical applications may include, but are not limited to, the development and discovery of drugs, their analytes and drug assays; disease discovery and detection tests; research and development of analytical testing in a variety of scientific fields and environments, and the like. Clinical applications may include, but are not limited to, DNA analysis; Neo-Natal screening; disease detection and diagnosis; drug, chemical or analyte testing and detection, and the like. While the foregoing uses are not meant to limit the scope of the invention, many additional uses of the present specimen collection slides exist and will be appreciated and understood in accordance with the description of the invention.

Since the present specimen collection slides are suitable for use with various applications, the specimens collected on such slides may also vary depending upon the end use of each collection slide. The specimen collected on the collection slides of the invention may be one or more purely biological samples, one or more purely chemical samples, or the specimens may be a combination of one or more biological and chemical samples. For instance, a purely biological sample may include, but is not limited to, blood, saliva, bodily secretions, organic matter, and the like. A purely chemical sample may include, but is not limited to, a drug, an analyte, an organic or inorganic chemical compound, and the like. A sample that includes both biological and chemical components, may include, but is not limited to, a blood sample being tested for presence of a drug, bodily secretions being tested for presence of an organic or inorganic chemical compound, such as, a contaminant (e.g., a poison), and the like.

While not meant to limit the invention, in one or more embodiments the present collection slides may be used to collect one or more dried blood spots. Dried blood spots (DBS) are used to transport a blood specimen from a source to the point of analysis. In so doing, small volumes of blood may be obtained from a source which may include, but is not limited to, an individual, patient, newborn, crime scene, laboratory sample, laboratory test animal, and the like. For instance, the blood sample may be obtained by a finger or heel stick of an individual. The amount of blood required for depositing on a single specimen collection slide may range from less than or equal to about 15 µL to greater than or equal to about 50 µL. One or more drops of the collected blood sample is/are deposited onto predefined location(s) on the filter paper media of the specimen collection slide, and allowed to dry. A typical drying time may range from less than or equal to about 2 hours to greater than or equal to about 3 hours. Once dried, the dried blood spots are stable on the present collection slides for 2-5 years, or even more.

In the specific application of using dried blood spots for clinical and/or preclinical applications, the analyte may be analyzed using liquid chromatography combined with mass spectroscopy (LC-MS or LC-MS/MS). For this type of application, the use of an internal standard is preferably included on a surface of the filtration media of the present collection slides, or throughout an entire thickness of such filtration media.

The use of an internal standard serves to normalize system response(s). In conventional approaches internal standard is mixed at a constant concentration with the nominal aliquot volume of sample. From that point on, errors in handling are compensated for by evaluating the response ratio of analyte to internal standard. For instance, if a transfer is made of a different volume of the sample mixture post internal standard addition, the ratio will provide a correction factor. The change in the internal standard response would indicate the difference in processing.

In Mass Spectrometer (MS) detection the need for internal standard is often critical since the MS monitors only the analyte mass transition while the effects of other interferences are not detectable from one sample to the next. Examples include dosing formulations of endogenous compounds that vary in their amount from sample to sample. These unseen components may suppress ionization of the analyte. By having an internal standard that coelutes with the analyte and is structurally similar, variations in ion suppression are factored out.

In clinical programs the internal standard is typically a stable labeled version of the analyte with deuterium substituted in hydrogen positions (Mass 1 replaced with Mass 2) and/or heavy carbon atoms (carbon 13 replacing carbon with 12 mass units) incorporated to give a different mass. Yet, the structure is identical with the analyte and so it coelutes and ionizes such analyte. For example, in a case where there are high levels of dosing vehicle PEG present in the first couple of time-points of a pharmacokinetic study, it may suppress the ionization by 80%. It does this both for the analyte and the stable labeled internal standard. The ratio of analyte to internal standard response remains the same, despite the 80% reduction in absolute response. This can still be compared with the standard curve response ratios, even though there is no suppression going on with the standards.

Again, in conventional approaches internal standard is added to the sample itself that is to be analyzed. In instances where the addition of internal standard is made at the point of use (i.e., added to the sample itself), a variety of methods may be implemented, depending on the choice and methods chosen by each individual end-user or laboratory. However, this can undesirably lead to inconsistencies when comparing results between different test or sample runs, or even between different laboratories involved in conducting a combined clinical study.

In accordance with the various embodiments of the invention, in order to avoid the inconsistencies in results of the conventional approaches of adding internal standard, the internal standard is added to the present specimen collection slides at the point of manufacturing such slides. That is, the internal standard of choice, for a specific project, is included on a surface of, or throughout an entire thickness of, the filtration media of the present collection slides at the point of manufacturing such slides.

At the point of manufacturing, a more precise method of adding the internal standard directly to the slides themselves may be implemented for all of the present collection slides, which may be used to support a specific clinical study. Again, with the use of dried blood spots for clinical and preclinical applications both the analyte and the internal standard on the slide may be stable for a number of years (e.g., for the life of the study or trial). By adding a preselected or desired internal standard directly onto or within the specimen collection slides of the invention (i.e., onto or within the filtration media of such slides) at the point of manufacture, the present specimen collection slides provide an improved degree of statistical control over the parameters involved and the credibility of performance of the end result.

In the one or more embodiments of the invention, the present specimen collection slides are at least composed of filtration media and a structural support for the filtration media. The filtration media is preferably capable of absorbing and retaining a liquid phase sample, which is applied and soaked into the fibers of the media and allowed to dry thereon and therein. The filtration media may be derived from several sources including, but not limited to, natural fibers, such as, wood fibers, cotton fibers, and the like. In one or more embodiments, wood fibers are preferred, while in other embodiments cotton linters are preferred, particularly for clinical and preclinical applications.

The structural support of the present specimen collection slides not only provide support for the filtration media retained therein, it also enables the easy and efficient implementation of the present slides with automated handling and processing systems. The structural support component of the present slides also provide protection against physical contact of the sample that is contained on the filtration media. Since the filtration media has sample on both sides, due to the soaking action, both sides of the filter media should be protected against intimate and direct contact with other or adjacent filter media also containing samples. In so doing, the filtration media of the present slides is sandwiched between at least two layers or pieces of structural support material.

The structural support material may be any material that provides rigidity for support, handling and integrity of the resultant slide, which is preferably easy to handle and preferably low cost. For instance, in one or more embodiments the structural support material may be a thermoplastic polymer, such as, polystyrene sheet stock, cut to size of the desired resultant slide. Polystyrene sheet stock is available in a variety of thicknesses and may be cut by shearing or die cutting. In other embodiments, the structural support may be made by injection molding using a material having sufficient rigidity upon completion of the final slide.

Figure 1A:
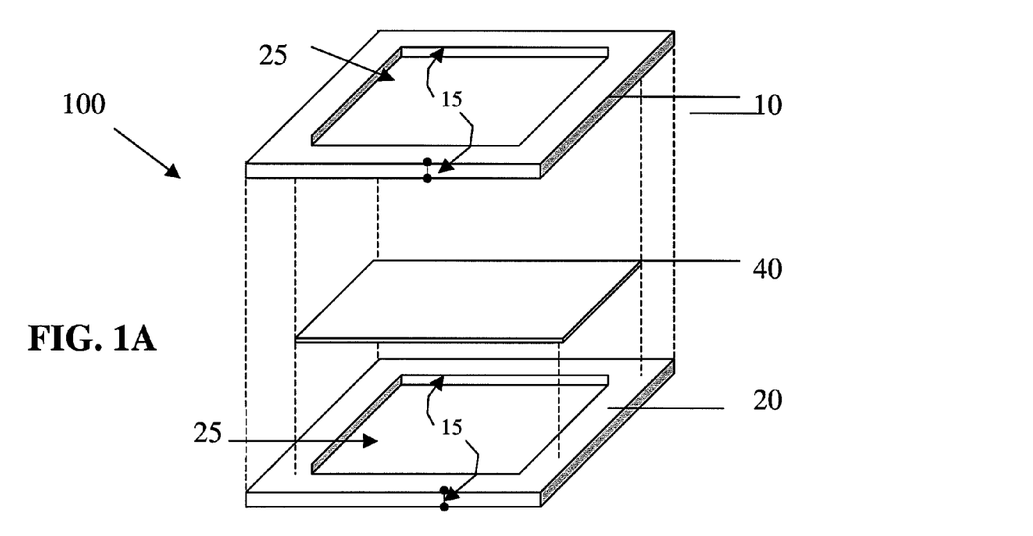
FIG. 1A is a perspective view showing components of a specimen collection slide according to one or more embodiments of the present invention.
Figure 1B:
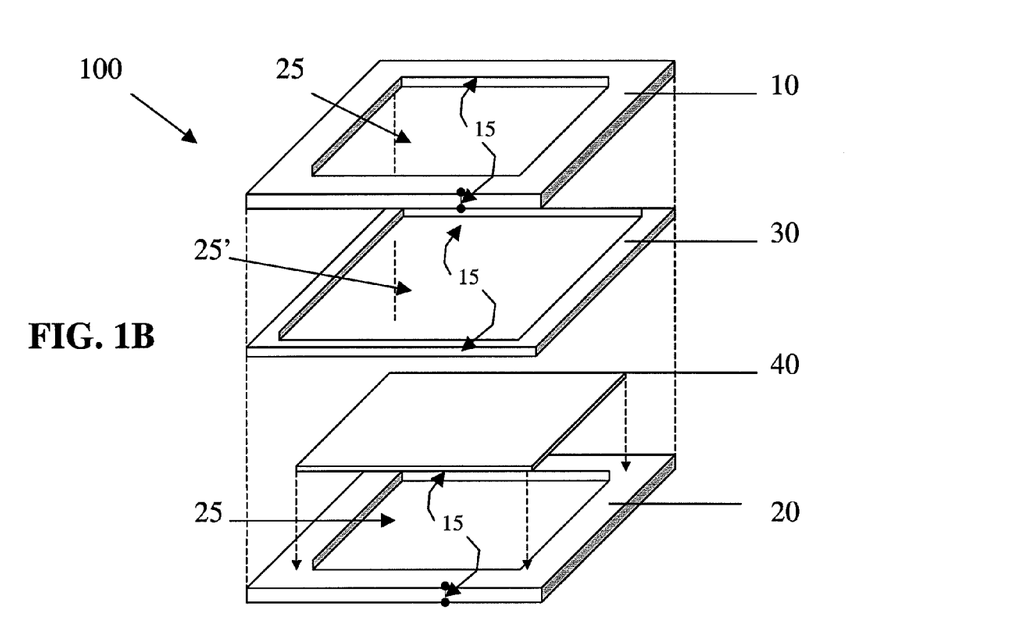
FIG. 1B is a perspective view showing components of a specimen collection slide according to one or more alternate embodiments of the invention.

For ease of understanding the invention, reference will now be made to the drawings wherein like numerals refer to like features of the invention. Referring to FIGS. 1A-B, the specimen collection slides 100 of the various embodiments of the invention at least include a pair of rigid frames 10, 20 with a sheet of filtration media 40 residing securely between the frames 10, 20. The filtration media 40 is encased between the first frame 10 and second frame 20. As is shown in FIG. 1B, in those embodiments wherein the rigid frames are cut or machined from a rigid sheet of material a third rigid frame 30 may reside between the first rigid frame 10 and the second rigid frame 20. This third rigid frame 30 also assists in holding and securing the filtration media 40 between the outer rigid frames 10, 20, as well as provides additional rigidity for assembly of the resultant slide.

Figure 1C:
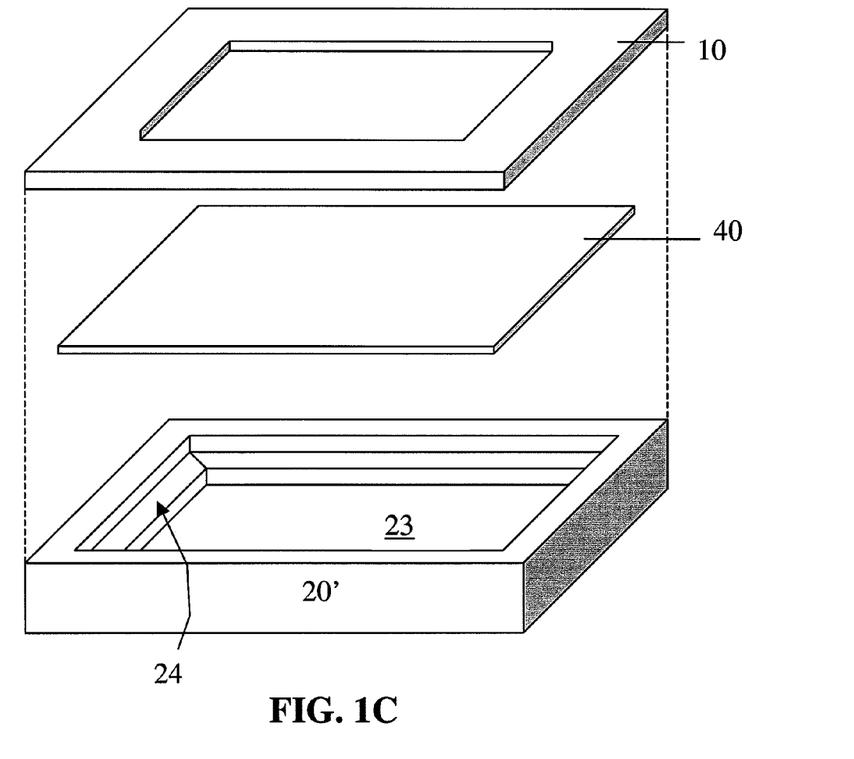
FIGS. 1C-D are perspective views showing components of a specimen collection slide according to still other embodiments of the invention.
Figure 1D:
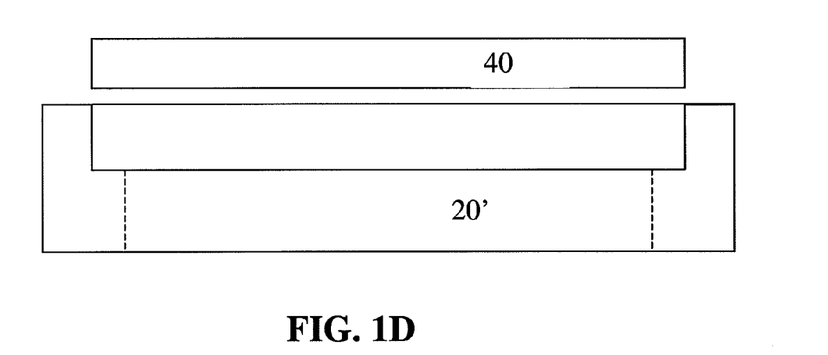

As is shown in FIGS. 1C-D, in other embodiments wherein the structural support is fabricated using injection molding techniques, the outer frame 20' may be fabricated as a single piece having an opening 23 adapted to receive and retain the filtration media 40 therein. This opening 23 preferably includes a ledge or lip area 24 capable of receiving and holding the filtration media inside the outer frame 20', such that, when the filtration media is residing therein, the filtration media and a top surface of the outer frame 20' are substantially planar with one another. The other outer frame 10 is similar to that described in relation to FIGS. 1A and 1B.

In all embodiments, the rigid frames (e.g., outer rigid frames 10, 20; or outer rigid frames 10, 30, 20; or outer rigid frames 10, 20') are all composed of a material having sufficient rigidity so as to prevent damage to the final specimen collection slide 100 (e.g., to prevent bending of such resultant slide). In those preferred embodiments including a third rigid frame 30, this third rigid frame 30 is also of a sufficiently rigid material that helps to prevent damage to the slide 100 and the sheet of filtration media 40 residing therein.

In accordance with the invention each frame 10, 20, 30 is provided with a sufficient thickness 15 both on its external edges and at edges inside its respective central opening 25. The thickness 15 of the frames 10, 20, 30 provide each frame with sufficient rigidity to prevent damage thereto, as well as to prevent damage to the overall resultant slide 100 when the frames are secured, bonded or welded together. The rigidity and thickness of each frame, and as such the overall resultant slide, also provides for ease of handling the slides as well as for ease of use and automation of each slide.

In one or more embodiments wherein the frames are fabricated by shearing or cutting, the material of the rigid frames 10, 20, and/or 30 may be a plastic material, such as, a thermoplastic polymer (e.g., polystyrene). For instance, the frames 10, 20, and/or 30 may be a polystyrene material of a high impact polystyrene sheet stock of mill rolls, whereby each rigid frame 10, 20, 30 is cut from the mill roll into predetermined dimensions as required to meet the desired dimensions of the final specimen collection slide 100. Each rigid frame may be cut from the mill roll in a controlled manner using a punch and die set, whereby repeatable dimensions of the cut frames 10, 20, 30 are preferably held to tolerances on the order of ±0.010 inches. Holding the repeatable dimensions to such standards is desirable to ensure reliable automated handling of the finished specimen collection slides 100 of the invention.

As shown in FIGS. 1A-B, the first 10, second 20 and third 30 rigid frames are all provided with a central opening 25 or window substantially at a middle of each frame. The first 10, second 20 and third 30 rigid frames also all have the same external dimensions of length and width. For purposes of illustrating the invention, in one or more embodiments the first 10, second 20 and third 30 rigid frames each may be composed of a high impact approximately 0.030 inch thick plastic material, such as, a thermoplastic polymer (e.g., polystyrene). The outer dimensions of each frame may be about 2.750 inches in length by about 2.500 inches in width, with the central opening 25 in each of the outer frames 10, 20 measuring about 1.750 inches by about 1.750 inches substantially in the middle of each frame to provide access to the filtration media sandwiched there-between.

The central opening 25 of each of the first (i.e., top) frame 10 and the second (i.e., bottom) frame 20 have substantially the same dimensions and provide access to the filtration media 40. However, the central opening 25' of the third rigid frame 30 is preferably sized to be larger than the openings in both the top and bottom frames 10, 20, as well as being slightly larger than the external dimension of the filtration media 40. That is, the external dimensions of the filtration media 40 exceed the dimensions of the access windows or openings 25 in each of the top and bottom frames 10, 20; however, are smaller than the external dimensions of such top and bottom frames 10, 20. As such, the third rigid frame 30 forms a cavity between the top and bottom frames 10, 20 to trap or capture the filtration media 40 without crushing any fibers thereof. Crushing of the filtration media fibers is undesirable since any crushing of fibers alters the density thereof, and as such, affects its ability to absorb liquid, which may be deleterious for end results of some applications.

In accordance with one or more preferred embodiments of the invention, by providing the third (i.e., middle) frame 30 with a thickness 15 that is greater than the thickness of the filter media 40 (which is retained and physically trapped by and within such frame 30), crushing of any fibers of such filter media is thereby prevented. If the filtration media has a greater thickness than the third member, then the amount of crushing is reduced by the difference in the relative thickness. As an alternative, a different thickness of material may be used for the third member 30.

Figure 4A:
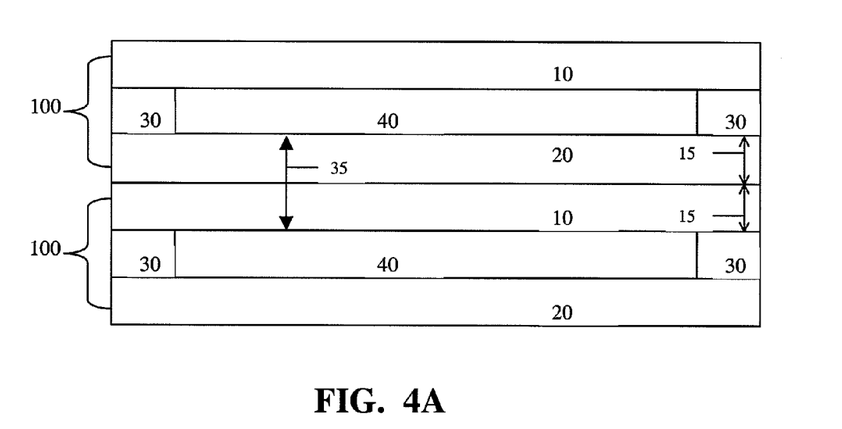
FIG. 4A shows a cross sectional view of the resultant specimen collection slide of FIG. 3A along line A-A'.
Figure 4B:
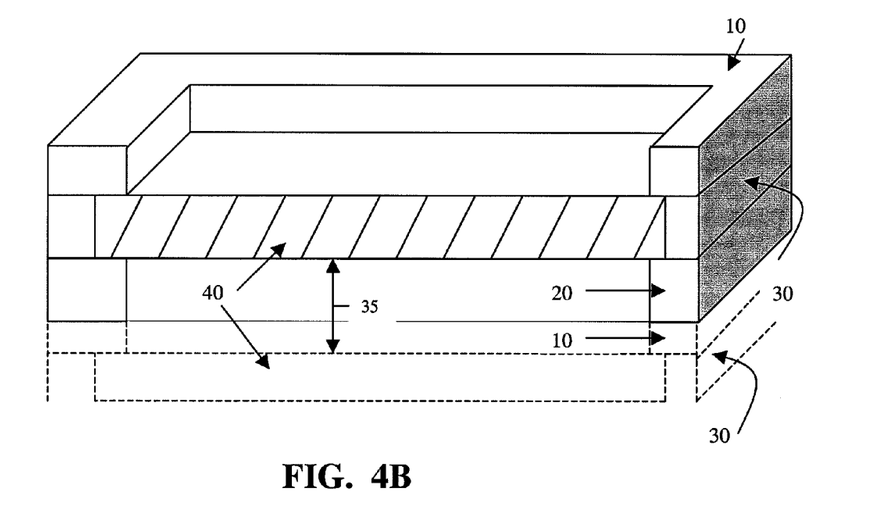
FIG. 4B shows a cross sectional view of a first slide 100 and a partial second slide of FIG. 4A showing the distance between adjacent sheets of filtration media.

Referring to the cross sectional views of FIGS. 4A-B along lines A-A' and B-B', respectively, the thickness 15 of each frame also provides each specimen collection slide 100 with the advantage that the filtration media 40 of adjacent slides 100 do not contact each other when two or more slides 100 are stacked one on top of the other. That is, when a first slide 100 is stacked upon a second slide 100, an empty cavity 38 is formed between exposed adjacent sheets of media. This empty cavity 38 has a thickness 35 approximately equal to the combined thicknesses 15 of a frame 10 of the first slide and a frame 20 of the second slide (minus any thickness of the sheet of filtration media that may be extending into the empty cavity 38). The empty cavity prevents the exposed adjacent sheets of filtration media 40 from contacting each other. This non-contact between adjacent sheets of filtration media 40 avoids cross contamination between specimens residing on these adjacent sheets of filtration media.

Unlike conventional paper or cardboard collection cards that are flimsy and too thin to prevent cross contamination between samples on media of adjacent paper or cardboard cards, the rigidity and thickness of the present specimen collection slides 100 provide for easily and efficiently maintaining specimen and/or sample integrity on adjacent slides both during use of such slides and for extended durations. In one or more embodiments, cross contamination prevention and rigidity of the slide 100 may be further enhanced by including the third frame 30, or even four or more frames (not shown), between the two outer frames 10, 20.

The filtration media 40 implemented in the various embodiments of the invention may vary depending upon the desired or specific application or use of the resultant slide 100. In one or more embodiments, the filtration media 40 may be a flexible fibrous material, such as a flexible paper material, that is capable of absorbing a specimen deposited thereon and allowing for such specimen to dry thereon. The filtration media 40 may have a wide range of characteristics that make it suitable for its intended purpose. For instance, filtration media 40 suitable for use in the various embodiments of the invention may have differing porosities, densities, thickness, physical characteristics and physical attributes; the media may be chemically or thermally treated; the media may be untreated media; and the like. Again for purposes of illustrating the invention, in one or more embodiments the filtration media may be a flexible paper material that has a thickness of about 0.017 inches, or a thickness of about 0.033 inches, and the like.

Referring to FIGS. 1A-3C, the desired filtration media 40 is provided between two or more rigid frames 10, 20, 30, et al. In so doing, the filtration media may be cut to a size that fits within and between the first rigid frame 10 and the second rigid frame 20, whereby the media 40 preferably resides at least beyond the edges of the central opening 25 of the outer frames 10, 20 as shown by the dashed arrows extending downward from the media 40 in FIGS. 1A-B. In preferred embodiments that include the third (middle) frame 30, the filtration media 40 has dimensions smaller than the opening 25' in this third frame 30 so that the media 40 may be trapped within such opening 25'. The filtration media 40 is secured between interior surfaces of the first and second rigid frames 10, 20, and in those embodiments including the third frame 30, is preferably secured within the central opening 25' of such third frame 30.

In one or more embodiments the filtration media 40 may be provided between the rigid frames using automated equipment so as not to contact or damage the delicate composition and framework of the media 40 itself, and/or to avoid contamination of such media 40 prior to the use thereof.

At this point, the first and second rigid frames 10, 20 are securely attached to each other using a technique that does not distort or bend any portion (e.g., the outer portions) of the resultant slide 100. For instance, the frames may be attached to one another by a variety of techniques including, but not limited to, ultrasonic welding, chemical bonding (e.g., through the use of a glue, adhesive, epoxy, etc.), thermal bonding, and the like, or even any combination thereof. By attaching the first and second rigid frames 10, 20 to one another the filtration media is physically trapped between such frames.

The filtration media 40 may be fixedly attached to both the first and second frames via the foregoing attaching techniques, or it may reside securely between the frames without being fixedly attached thereto. By not fixedly attaching the filtration media 40 to the first and second frames, contamination of the filtration media by the bonding components and/or techniques may be avoided. For example, in instances where an adhesive is used to bond the rigid frames together any contamination by the adhesive onto the filtration media may detrimentally affect the usefulness of such media and the overall usefulness of the resultant slide. As such, contact between the adhesive and the filtration media is avoided.

In embodiments including one or more additional frames 30, et al. between the first and second rigid frames 10, 20, the filtration media 40 may be cut so that it fits securely inside the opening 25 within the middle frame 30. Alternatively, the filtration media 40 may be cut so that it extends just beyond the borders of the opening 25. These one or more additional rigid frames 30 between the outer first and second frames 10, 20 provide additional support, rigidity and height between adjacent filtration media 40 of adjacent slides 100. The additional frame 30 also assists in trapping or containing the filtration media in the slide without causing excessive crushing of the filtration media, and in particular, without crushing the fiber content of the media. Again, excessive damage to the filtration media may be detrimental since it would hinder the media's capabilities of absorbing any specimen deposited thereon.

In those preferred embodiments that include the third middle frame 30, the third frame 30 may be securely attached to interior surfaces of both the first and second rigid frames 10, 20 (as shown in FIG. 1B) so that the filtration media 40 is retained between these rigid frames. Again, a variety of attaching techniques may be implemented in attaching the plurality of frames 10, 20, 30 together including, for instance, ultrasonic welding, bonding, gluing, and the like. Preferably, in various embodiments the two or more frames are permanently bonded together. In one or more preferred embodiments the first 10, second 20 and third 30 rigid frames are all composed of the same homogenous material (e.g., polystyrene) such that they may be securely bonded using ultrasonic welding to form the resultant slide 100. Ultrasonic welding of these frames also prevents the need for bonding using solvent based glue and/or adhesives that may contact and detrimentally affect the properties of the filtration media, and as such, any downstream end results.

Again, in embodiments such as those shown in relation to FIGS. 1C and 1D, at least one of the outer frames (i.e., frame 20') may be provided with an opening 23 and internal ledge or lip area 24 for receiving the filtration media. This ledge or lip area 24 essentially avoids the need for middle frame 30 since the external portion of such ledge or lip area replaces the middle frame 30. The frame 20' has a thickness at its outer edges that provides the frame 20' with sufficient rigidity to avoid bending and/or damage to the resultant slide upon assembling and attaching the outer frame 20' to another outer frame 10.

FIGS. 2A-3C show alternate views of different embodiments of the present specimen collection slides 100. Referring to the perspective views of FIGS. 2A-B and 3A-B different embodiments are shown whereby each slide 100 of the invention has two or more rigid frames 10, 20, 30 securely holding and retaining a filtration media 40 there between. The filtration media 40 is exposed at this first surface (e.g. a top surface) of the collection slide 100 and is recessed within the slide 100 from a top plane surface of the outer frame 10 into the slide 100 to a depth substantially equal to the thickness 15 of such outer frame 10.

Figure 2A:
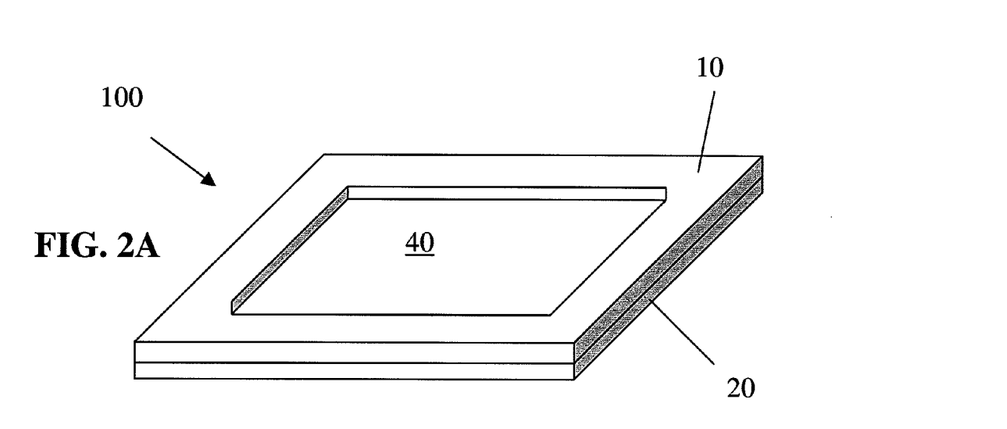
FIGS. 2A-C show perspective top and bottom views of the resultant specimen collection slide of FIG. 1A.
Figure 2B:
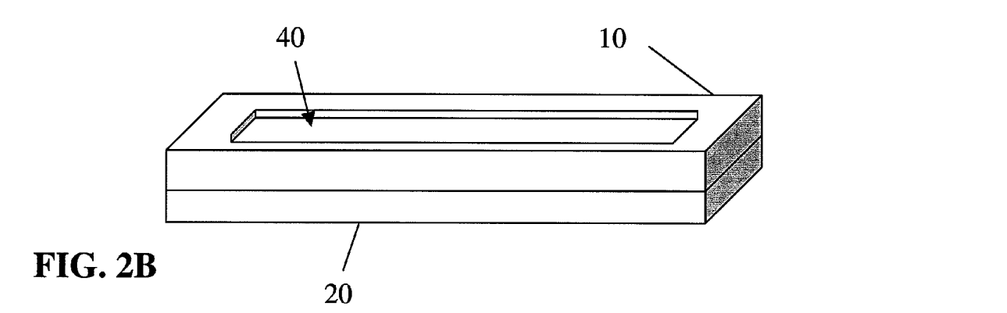
Figure 2C:
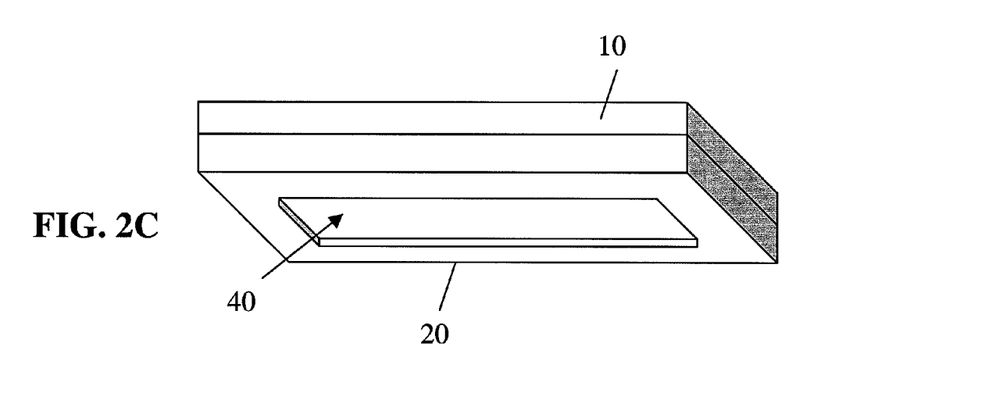
Figure 3A:
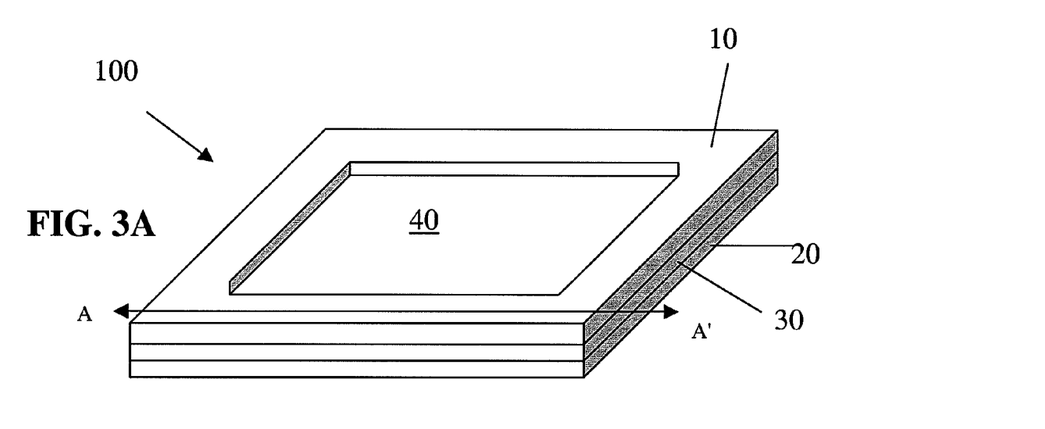
FIGS. 3A-C show perspective top and bottom views of the resultant specimen collection slide of FIG. 1B
Figure 3B:
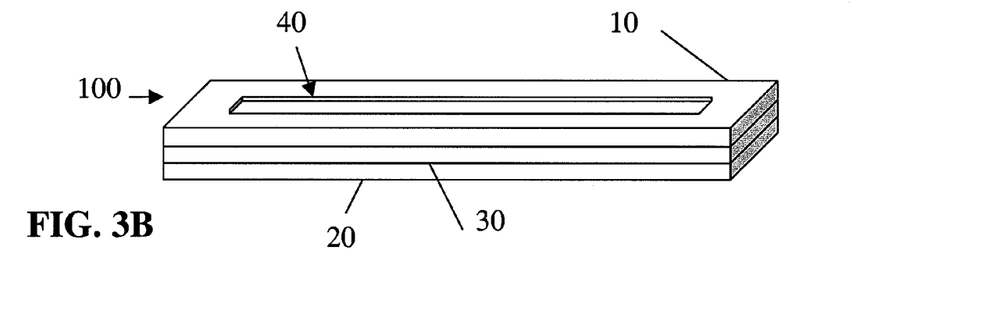
Figure 3C:
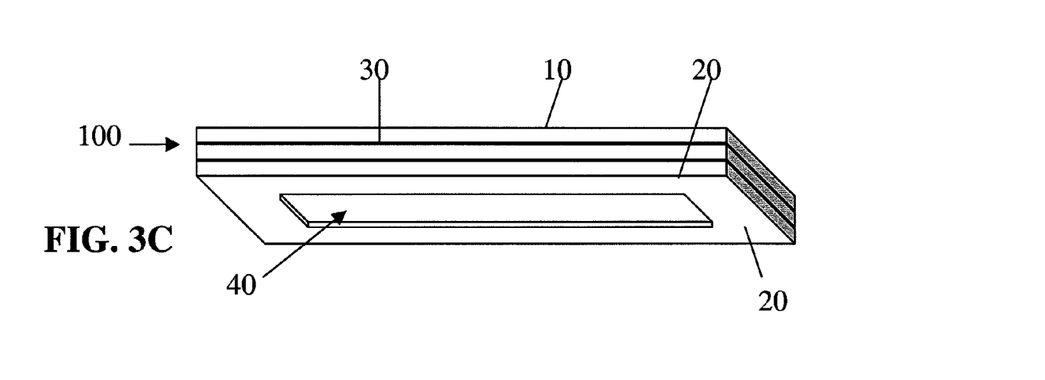

FIGS. 2C and 3C show perspective views of different slides 100 of the invention from a second surface (e.g. a bottom surface) of the collection slide 100. The filtration media 40 is also exposed at this second surface, and is recessed within the slide 100 from an outer plane surface of the outer frame 20 into the slide 100 to a depth substantially equal to the thickness 15 of such outer frame 20. Again, in this manner when the various collection cards 100 of the invention are stacked, or contact one another (as shown in FIG. 4B along line B-B'), an empty cavity 38 is formed between exposed adjacent sheets of media that has a thickness 35 approximately equal to the combined thicknesses 15 of the adjacent frames on different slides 100 (minus any thickness of filtration media extending into the empty cavity 38).

Figure 5A:
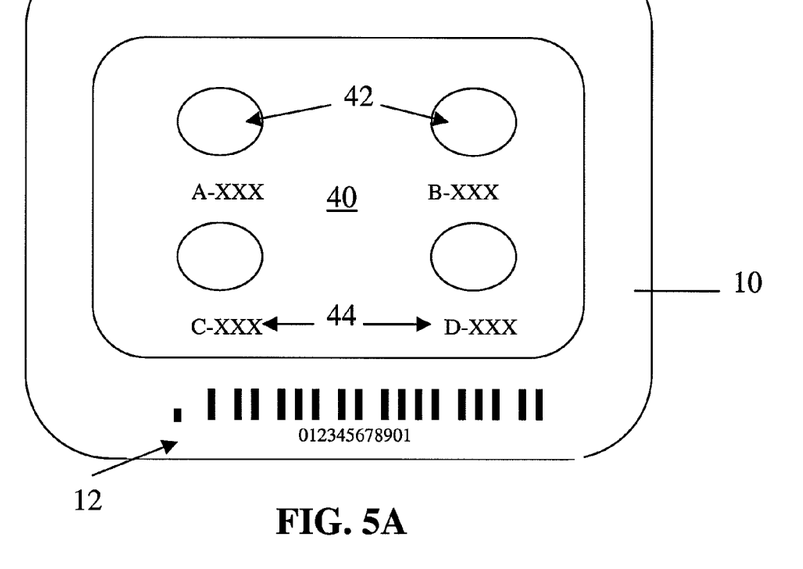
FIG. 5 shows top plan view of a specimen collection slide in accordance with one or more embodiments of the invention.
Figure 5B:
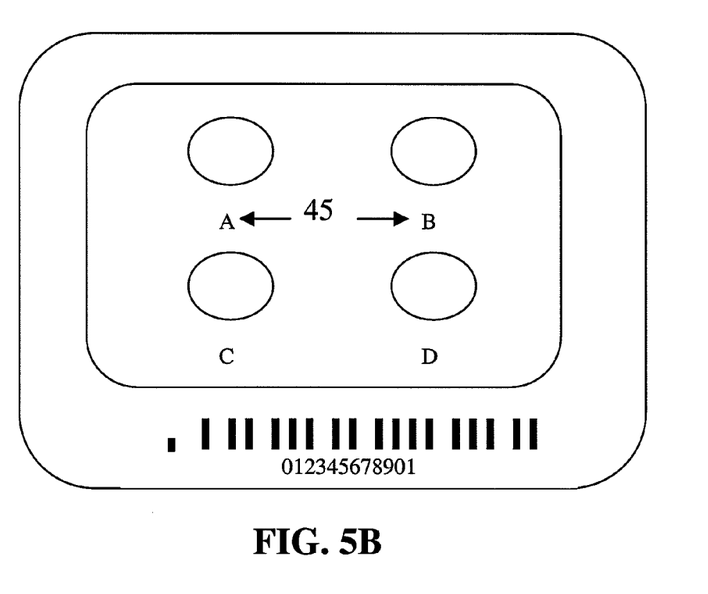

FIGS. 5A and 5B show top plan views of one or more embodiments of specimen collection slides 100 in accordance with the invention. The slide 100 is shown having filtration media 40 exposed within a recessed cavity of the rigid frame 10. It should be appreciated that due to the thickness of the outer frames 10, 20 both sides of the slide 100 (i.e., top/bottom, upper/lower, etc.) have filtration media 40 within recessed cavities of such slides 100 at the position where the central opening 25 resides.

A portion of the specimen collection slide 100 is provided with a first unique identifier 12 that identifies and distinguishes each slide 100 from other slides 100 having their own respective unique identifiers. In one or more embodiments, the first unique identifier 12 may reside on an exterior surface of at least one of the outer rigid frames 10, 20. The unique identifier 12 may be provided on the slide 100 soon after such slide has been manufactured, and is preferably not repeated for any subsequently made slides. In various embodiments the unique identifier 12 may be a 12 digit Code 128 barcode, which is an alpha-numeric code capable of providing numerous unique identifications. Each unique identifier 12 may be permanently affixed to its respective slide 100 by methods including, but not limited to, printing, embossing, embedding, engraving, staining, and the like, or even combinations thereof. The unique identifier 12 preferably remains with the slide 100 from manufacture, to point of specimen source, to discard of the slide.

The unique identifier 12 on each slide 100 is different and distinct from all other identifiers 12 on any other slide, such that, each unique identifier 12 (i.e., barcode number) will only be designated once (i.e., the same unique identifier 12 (i.e., barcode number) will never be printed twice or assigned to another slide). In this manner, each unique identifier is universally distinct from other unique identifiers, making the collection of data nationwide, or even worldwide, much easier, efficient, cost effective and reliable.

Currently in the dried blood spots industry manufacturers of cards each provide their own identifier on their respective cards, whereby once a testing lab (e.g., the CDC) receives the various manufacture cards the lab often needs to include a further identifier on the card to provide a universal code across all cards received for the study. In accordance with the present invention such tedious and time-consuming tasks are avoided since each slide 100 of the various embodiments of the invention is provided with a universally distinct unique identifier at the point of manufacture. These universally distinct unique identifiers 12 also help in maintaining privacy of any supplier(s) of samples (e.g., patients) on the slides since each unique identifier is assigned to a specific supplier (patients). This makes it much easier, as compared to current practices, to completely divorce privacy data from generic database information.

The filtration media 40, which again may be pretreated with an internal standard, is provided with a plurality of predefined delineated locations 42 for receiving the specimen of choice. These delineated locations 42 may be any means that indicates where a specimen should be deposited onto the filtration media, or where a specimen has already been deposited onto the media by an automated handling system. For instance, while not meant to limit the invention, FIG. 5A shows the predefined locations 42 as four delineated circles permanently printed on at least one surface of the media, or optionally both surfaces of the media. Referring to FIG. 5A each predefined location 42 on the filtration media 40 may also be given its own unique identification 44 that distinguishes each delineated location 42 on the slide 100 from the other delineated location(s) 42 on the same slide 100, or even from one or more delineated locations 42 on different slides 100. This unique identification 44 may also be a plurality of digits using an alpha numeric 128 barcode. As such, each individual specimen collection slide 100 is provided with a primary unique identification (i.e., first unique identifier 12) and any number of sub- or secondary unique identifiers (i.e., unique identifications 44).

By providing each predefined location 42 on a single on filtration media 40 with its own unique identification 44, the present slides 100 are able to receive and retain a number of different specimen sources on a single slide 100. For instance, an entire family may be able to store dried blood spots on a single slide 100, which may be useful in genetic testing and screening, disease detection and screening, paternity testing, and the like. As an example, dried blood spots from each of a mother, father and new born may be deposited and retained on a single slide 100 for later use to test for and/or verify paternity. As another example, a drug and its various analogs may be deposited and stored on a single slide 100, which may be important for research and development of new drug discoveries. While the foregoing examples are described to help understand the novel concepts of the invention, it should be appreciated and understood that a number of possibilities exist for storing different specimens on a single slide 100.

In one or more embodiments, each unique identification 44 may be linked to the first unique identifier 12 that distinguishes each slide from other slides. An end-user of the slides 100 may further cross link the first unique identifier 12, alone or together with the unique identifications 44, to other processing identifiers that may be attached to the slide. For instance, specific sample processing identifiers may be attached to the slide at the point of sample source (e.g., a sticky back label that may include any one or more of the following: a person's name, date, time of sample acquisition, alpha characters and numeric values, etc.) in combination with the unique identifier 12 and/or unique identifications 44. In this manner, all of these identifiers help to distinguish a given slide 100 from other slides, and identify the specimens stored on such given slide from the point of obtaining the specimen sample to discard of the slide. A data log may be generated that cross links the unique identifier 12, unique identifications 44, and specific sample processing identifiers, alone or in any combination thereof, to a given slide and stored at a facility with such slide to ensure proper identification of the slide and the dried samples stored thereon.

Alternatively, referring to FIG. 5B, rather than providing a number of different specimen sources on a single slide 100 numerous samples of a single specimen may be provided onto the filtration media 40 of the present slides 100. This is often essential for recalling and retesting any given specimen. For instance, referring to FIG. 5B the four different predefined locations 42 may be provided with a single dried specimen whereby these numerous spots allow for one spot to be initially used, one to lose and two to be recalled for further testing (e.g., for result confirmation testing). This allows for the easy and accurate retesting of a previously tested specimen.

As discussed above, once the specimen collection slide 100 is fabricated it is provided with a specimen in or on its predefined delineated locations 42. The specimens collected and dried onto the slide may vary depending upon the specific end use of such specimen collection slide. These specimens may be one or more purely biological samples, one or more purely chemical samples, or the specimens may be a combination of one or more biological and chemical samples. The dried specimens may be stored on the present collection slides for 2-5 years, or even more if a stabilizer or enhancer is added either to the sample itself or the filtration media.

Figure 6A:
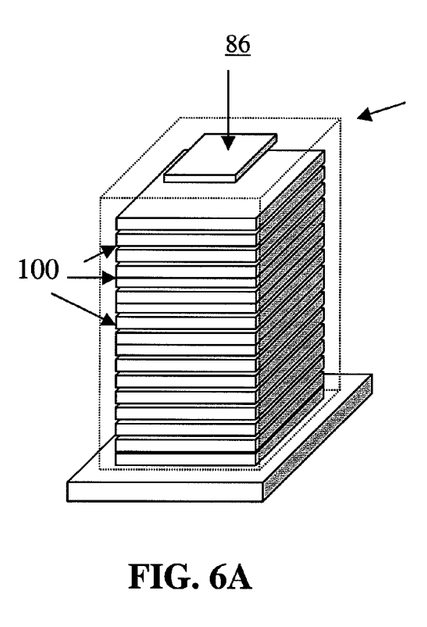
FIGS. 6A-B show perspective views of a cassette holder of the invention for retaining one or more specimen collection slides in accordance with the various aspects of the invention.
Figure 6B:
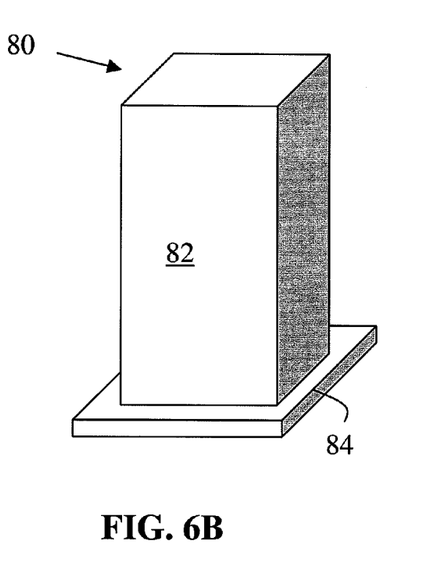

Once the specimen collection slide 100 has one or more dried specimens on the filtration media 40, these slides with their respective dried specimens must be stored in a dry environment to maintain and preserve specimen viability. Referring to FIGS. 6A-B a cassette holder 80 is fabricated that is capable of holding and storing a number of such slides 100. Each cassette holder 80 is fabricated using known techniques, such as injection molding, and is provided with dimensions sufficient for either manually or mechanically loading and unloading of a number of slides 100 therein.

The cassette holder 80 at least includes a bottom portion 84, a removable lid 82 and a desiccant 86 to maintain a dry environment for the slides 100 within the cassette holder 80. Each cassette holder 80 may also be provided with its own unique identifier (e.g., a barcode) that is linked to the slides 100 residing therein for easy, quick and efficient recall of any slide 100. When in ambient conditions for use, the removable lid 82 may cover the slides 100 residing within the cassette holder 80, but remains unsealed, to maintain a dry environment for the slides 100 within the cassette holder 80. The desiccant 86 is in an air permeable package and is equilibrated to maintain the contents within the cassette holder 80 in a dry condition when the cassette holder is in ambient room conditions for short periods of time (e.g., more or less than about 12 hours). When the cassette is returned to dry room storage conditions, for extended periods, the cassettes internal desiccant package 86 will re-equilibrate to the dry room conditions. Thus, it performs its requirement of maintaining a dry environment in the event the cassette is again moved to ambient conditions for short term processing of the cassette's slide contents.

The dessicant within the cassette holder 80 is chosen such that it preferably re-equilibrates to its surrounding conditions by itself (i.e., without any external means). That is, when in a humid environment, such as when the cassette is in ambient conditions, it will attract and absorb water vapor to keep the contents of the cassette dry. This will occur until the desiccant has reached equilibrium with the surrounding water vapor. When returned to dry room storage conditions, the desiccant will give up the contained water vapor until it is equilibrated with the dry room conditions. Thus, in essence, it is recharged to a dry condition, prior to its next move to ambient conditions.

During use the specimen collection slides 100 of the various embodiments of the invention may be automatically handled whereby a dried specimen spot is punched from the filtration media and eluted for analysis. The rigidity of the present slides 100 allows for the easy, fast and efficient automated handling thereof, and aids in the prevention of damage to the remaining filtration media and specimens residing thereon, as well as prevents damage to the overall slide itself. Since a variety of different filtration medias may be provided within the present slides, as well as a variety of different specimens dried on such differing media, the punched specimens may be subjected to various analytical procedures. As such, the slides 100 of the invention are suitable for use with a variety of currently available and future developed automated clinical and preclinical applications.

For instance, the various specimen collection slides 100 of the invention may be implemented in the research and development of new drug discoveries or new disease testing procedures, screening tests (e.g., neo-natal screening for congenital and inherited metabolic disorders), DNA (genetic) analyses, forensic studies (e.g., crime scene investigations, deceased identification or cause of death, etc.), immunologic studies, nutritional evaluations (e.g., in adults, children, newborns, non-humans, etc.), disease/disorder detection or diagnosis, quality assurance and quality control procedures, drug detection, and the like.

A process flow of fabricating specimen collection slides 100 in accordance with one or more preferred embodiments of the invention follows. A fully automated instrument is provided to fabricate the present slides 100 in a fully automated production line.

The automated instrument may be a walking beam system that includes an AC gearmotor with a variable frequency drive that drives the walking beam through a heavy-duty cam. As the cam drive rotates, the walking beam moves up, lifting the slide 100 components at a number of different processing stations simultaneously, and transferring them forward to the next station. The beam then drops down depositing the components on the next station to complete the next sequence of the assembly. As the beam drops down, a signal is generated that starts the action on each station. Each of the different stations runs independently. When each has completed its task, it provides a completion signal. When all of the stations report completions, the walking beam restarts with another cycle. Operating logic exists at each station for performing and completing its respective tasks, whereby the entire processing line runs automatically with minimal operator intervention.

Each of the automated instrument's different stations has independent control sequences that will be started by energizing a control relay. When the station sequence is complete, the control relay will drop out providing a normally closed contract. In one or more embodiments the process starts by energizing the drive system to apply power to the main drive motor, which moves the cam to put the walking beam to its start position to activate each station.

The first station preferably admits air to push the slide front layer (e.g., layer 10) from an incoming stacker into a first position ("position A") of the walking beam. Actuation of an optical sensor indicates that the front layer is in position A of the walking beam. If this front layer is not detected, a failure light is illuminated and the process repeated, whereby if the front layer continues to not be detected then further action on the instrument is prohibited.

The process flow continues by moving the slide middle layer (e.g., layer 30) into a second position ("position B") of the walking beam. Again, illumination of an optical sensor indicates whether or not the middle layer is at position B. The automated instrument is then provided with the filtration media.

The filtration media roll is received and threaded on a core through the instrument to its initial starting position without damaging (e.g., compressing, tearing, distorting, etc.) any portion of the filtration media. The filtration media roll may be manually threaded through to the knife. Motion and unwinding of the filtration media roll into the instrument is automatically controlled to enable precise cutting of the media into filtration media layers 40 of the slides 100. Preferably, free hanging loops control the infeed of the media into the instrument so as to eliminate tension in the roll of filtration media, whereby an electronic beam type sensor monitors the bottom of the loop such that when the beam is broke infeed of the media is stopped. The cut piece of filter media 40 is moved forward to the walking beam third position ("position C").

The slide bottom layer (e.g., layer 20) is input from an incoming stacker into a fourth position ("position D") of the walking beam. As discussed above, illumination of an optical sensor indicates whether or not the bottom layer is at position D.

After completing the above sequence, it is verified that the various layers to be provided within the assembly are present prior to welding the slide together. These layers are preferably in alignment with one another prior to welding. The presence (or absence) of each layer may be detected using an electrical solenoid that drops a measuring pin down on the finished surface to detect the presence or absence of each of the specific layers. Once it is determined that all parts are present, the assembly is moved to another station where the slide front, middle and bottom layers are ultrasonically welded together. A control relay starts an internal control sequence for welding the frames together. Preferably the welding is performed from the bottom side to prevent marking the barcode area on the front face.

At the next couple of stations a control relay actuates the barcode printing sequence controller, and then another control relay turns on the pad printer operating sequence. The completed slide is then inspected at another station, and if it is found to be defective, the defective slide is rejected. The slides are offloaded at another station from the automatic instrument into a cassette holder 80 of the invention. Once a predetermined number (e.g., 100) of slides have been loaded into the cassette holder 80, the cassette holder 80 is removed from the instrument (i.e., either manually or automatically). The instrument may be equipped to hold a number of cassette holders for the simultaneous or concurrent placement of slides therein.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A specimen collection slide comprising:
a top rigid layer having a first central opening;
a middle rigid layer having a second central opening larger than the first central opening;
a filtration media layer for retaining a sample residing entirely within the second central opening of the middle rigid layer, the middle rigid layer protecting said filtration media from damage thereto;
a bottom rigid layer having a third central opening substantially the same size as the first central opening;
one or more delineated locations on the filtration media layer that identify where one or more samples are to be deposited onto the filtration media, the first central opening of the top rigid layer and the third central opening of the bottom rigid layer exposing portions of first and second sides of the filtration media layer to expose the one or more delineated locations for deposition of said one or more samples directly onto said one or more delineated locations,
an external perimeter of said filtration media layer located on said first and second sides, the external perimeter of the first side of the filtration media contacts a portion of the top rigid layer while the external perimeter of the second side of the filtration media contacts a portion of the bottom rigid layer both for securing said filtration media layer within the specimen collection slide, whereby the top, middle, and bottom rigid layers have the same external dimensions, and are securely attached together without damaging the filtration media by attaching the top rigid layer to the middle rigid layer on a first side thereof, and the middle rigid layer is attached at a second side thereof to the bottom rigid layer, said top, middle, and bottom rigid layers being bonded together or ultrasonically welded together to provide the specimen collection slide with a thickness sufficient for handling.

2. The specimen collection slide of claim 1 wherein the first, second and third rigid layers provide the specimen collection slide with rigidity and the thickness sufficient for handling by an automatic handling specimen collection slide instrument.

3. The specimen collection slide of claim 1 further including the filtration media layer having an internal standard.

4. The specimen collection slide of claim 1 wherein the first, second and third rigid layers comprise an identical material, and have substantially identical external dimensions.

5. The specimen collection slide of claim 4 wherein the first, second and third rigid layers comprise a plastic material.

6. The specimen collection slide of claim 1 further including a unique identifier on each said specimen collection slide for distinguishing one specimen collection slide from another.

7. The specimen collection slide of claim 1 whereby the specimen collection slide is a first specimen collection slide in contact with a second specimen collection slide, one of the plastic layers of the first specimen collection slide contacts one of the plastic layers of the second specimen collection slide to provide a distance between adjacent filtration media layers of the first and second specimen collection slides, the distance preventing contact between said adjacent filtration media layers and preventing cross-contamination of any samples residing on said adjacent filtration media layers.

8. The specimen collection slide of claim 1 wherein the filtration media layer of the specimen collection slide contains one or more dried samples selected from the group consisting of biological samples, chemical samples, or combinations thereof.

9. The specimen collection slide of claim 1 wherein the filtration media layer has one or more cut locations that identify where one or more samples are to be deposited onto the filtration media from the first central opening or the third central opening.

10. A method of fabricating a specimen collection slide comprising:
providing a first rigid layer having a first central opening;
providing a second rigid layer having a second central opening larger than the first central opening;
positioning a filtration media layer entirely within the second central opening of the second rigid layer to protect the filtration media;
providing a third rigid layer having a third central opening substantially the same size as the first central opening;
aligning the first, second and third rigid layers so that the second rigid layer and the filtration media layer reside between the first and third rigid layers, the first, second and third rigid layers having the same external dimensions, the filtration media layer having an external perimeter whereby a first side of the external perimeter contacts a portion of the first rigid layer while a second side of the external perimeter contacts a portion of the third rigid layer for securing said filtration media layer between said first rigid layer and said third rigid layer; and securing the first, second and third rigid layers together in a stack without damaging the filtration media by bonded together or ultrasonically welded together said first, second and third rigid layers, whereby the first central opening and the third central opening expose opposing surfaces of the filtration media layer to external environment.

11. A specimen collection slide comprising:
a top rigid layer having a first central opening;
a middle rigid layer having a second central opening larger than the first central opening;
a filtration media layer for retaining a sample residing entirely within the second central opening of the middle rigid layer, the middle rigid layer protecting said filtration media from damage thereto;
a bottom rigid layer having a third central opening substantially the same size as the first central opening;
an external perimeter of said filtration media layer, whereby a first side of the external perimeter contacts a portion of the top rigid layer while a second side of the external perimeter contacts a portion of the bottom rigid layer for securing said filtration media layer between said top rigid layer and said bottom rigid layer; and
a unique identifier on each said specimen collection slide for distinguishing one specimen collection slide from another,
whereby the top, middle, and bottom rigid layers have the same external dimensions, and are securely attached together in a stack without damaging the filtration media to provide the specimen collection slide with a thickness sufficient for handling, the filtration media layer residing within the middle rigid layer not contacting any other media.

12. The specimen collection slide of claim 11 further including the filtration media layer having an internal standard.

13. The specimen collection slide of claim 11 wherein the first, second and third rigid layers comprise an identical material, and have substantially identical external dimensions.

14. The specimen collection slide of claim 11 wherein the first, second and third rigid layers comprise a plastic material.

15. The specimen collection slide of claim 11 whereby the specimen collection slide is a first specimen collection slide in contact with a second specimen collection slide, one of the plastic layers of the first specimen collection slide contacts one of the plastic layers of the second specimen collection slide to provide a distance between adjacent filtration media layers of the first and second specimen collection slides, the distance preventing contact between said adjacent filtration media layers and preventing cross-contamination of any samples residing on said adjacent filtration media layers.

16. The specimen collection slide of claim 11 wherein the filtration media layer of the specimen collection slide contains one or more dried samples selected from the group consisting of biological samples, chemical samples, or combinations thereof.

17. The specimen collection slide of claim 11 wherein the filtration media layer has one or more delineated locations that identify where one or more samples are to be deposited onto the filtration media from the first central opening or the third central opening.

18. A specimen collection slide consisting essentially of:
a top rigid layer having a first central opening;
a bottom rigid layer having a second central opening substantially the same size as the first central opening; a middle rigid layer having a third central opening that is larger than both the first central opening and the second central opening, the middle rigid plastic layer residing directly between the top and bottom rigid plastic layers;
a primary unique identifier residing on the top rigid plastic layer that distinguishes the specimen collection slide from other specimen collection slides;
a filtration media layer for retaining a sample residing entirely within the third central opening of the middle rigid layer and contacting a portion of interior surfaces of both the top and bottom rigid plastic layers whereby:
a first perimeter on a first side of the filtration media layer contacts a portion of an interior surface of the top rigid plastic layer, and
a second perimeter on a second side of the filtration media layer contacts a portion of an interior surface of the bottom rigid plastic layer;
a plurality of predefined delineated locations on the filtration media layer each indicating locations where one or more samples are to be deposited; and
a plurality of secondary unique identifiers on the filtration media layer each identifying and distinguishing different ones of said redefined delineated locations from each other;
whereby the top, bottom and middle rigid layers have substantially identical external dimensions, and are directly and securely attached together without damaging the filtration media to provide the specimen collection slide with a thickness sufficient for handling,
whereby at least the first central opening of the top rigid plastic layer exposes a portion of the filtration media layer, the plurality of predefined delineated locations, and the plurality of secondary unique identifiers for access thereto, and
whereby together said primary unique identifier and said plurality of secondary unique identifiers enable both accurate sample identification for said sample deposited within each said plurality of predefined delineated locations and subsequent recall of said specimen collection slide for accurate processing of any remaining ones of said plurality of predefined delineated locations retaining said sample.

19. The specimen collection slide of claim 18 wherein the primary unique identifier is a universally distinct unique identifier that is permanently provided on the top rigid layer of the specimen collection slide at the point of manufacture to maintain sample identification consistency for assuring a positive sample identification from source to discard.

20. The specimen collection slide of claim 18 wherein the first, second and third rigid layers comprise a rigid plastic material, wherein the thickness of the specimen collection slide is sufficient for automated handling.

21. The specimen collection slide of claim 20 whereby the specimen collection slide is a first specimen collection slide in contact with a second specimen collection slide, one of the rigid plastic layers of the first specimen collection slide contacts one of the rigid plastic layers of the second specimen collection slide to provide a distance and an empty cavity between adjacent filtration media layers of the first and second specimen collection slides that prevent contact between said adjacent filtration media layers and prevent cross-contamination of any samples residing on said adjacent filtration media layers.

22. The specimen collection slide of claim 18 wherein the filtration media layer of the specimen collection slide contains a number of different dried samples thereon, whereby together said primary unique identifier and said plurality of secondary unique identifiers enable each of said different sample specimens to be uniquely identified from one another and removed from said specimen collection slide.

23. A specimen collection slide consisting of:
a top rigid plastic layer having a first central opening;
a bottom rigid plastic layer having a second central opening substantially the same size as the first central opening;
a middle rigid plastic layer having a third central opening that is larger than both the first central opening and the second central opening, the middle rigid plastic layer residing directly between the top and bottom rigid plastic layers;
a primary unique identifier residing on said top rigid plastic layer that distinguishes said specimen collection slide from other specimen collection slides;
a filtration media layer for retaining a sample and having external dimensions larger than both the first central opening and the second central opening, the filtration media layer residing entirely within the third central opening of the middle rigid plastic layer and contacting a portion of interior surfaces of both the top and bottom rigid plastic layers whereby:
a first perimeter on a first side of the filtration media layer contacts a portion of an interior surface of the top rigid plastic layer, and
a second perimeter on a second side of the filtration media layer contacts a portion of an interior surface of the bottom rigid plastic layer;
a plurality of predefined delineated locations on the filtration media layer each indicating where the sample is to be deposited onto the filtration media; and
a plurality of secondary unique identifiers on the filtration media layer each identifying and distinguishing different ones of said predefined delineated locations from each other, whereby the top, bottom and middle rigid plastic layers have substantially identical external dimensions, and are directly and securely attached together without damaging the filtration media to provide the specimen collection slide with a thickness sufficient for handling,
whereby at least the first central opening of the top rigid plastic layer exposes a portion of the filtration media layer, the plurality of predefined delineated locations, and the plurality of secondary unique identifiers for access thereto, and
whereby together said primary unique identifier and said plurality of secondary unique identifiers enable both accurate sample identification for said sample deposited within each said plurality of predefined delineated locations and subsequent recall of said specimen collection slide for accurate processing of any remaining ones of said plurality of predefined delineated locations retaining said sample.

24. The specimen collection slide of claim 23 wherein the first, second and third rigid layers comprise an identical material, and have the same external dimensions.

25. The specimen collection slide of claim 23 whereby the specimen collection slide is a first specimen collection slide in contact with a second specimen collection slide, one of the plastic layers of the first specimen collection slide contacts one of the plastic layers of the second specimen collection slide to provide a distance and an empty cavity between adjacent filtration media layers of the first and second specimen collection slides, the distance and empty cavity preventing contact between said adjacent filtration media layers and preventing cross-contamination of any samples residing on said adjacent filtration media layers.

* * * * *

UNITED STATES PATENT AND TRADEMARK OFFICE
CERTIFICATE OF CORRECTION

| | | |
|---|---|---|
| PATENT NO. | : 9,575,084 B1 | Page 1 of 1 |
| APPLICATION NO. | : 12/868229 | |
| DATED | : February 21, 2017 | |
| INVENTOR(S) | : Thomas W. Astle | |

It is certified that error appears in the above-identified patent and that said Letters Patent is hereby corrected as shown below:

In the Specification

In Column 9, Line 23, delete "18" and substitute therefore -- 1B --

In the Claims

In Column 20, Line 26, delete "redefined" and substitute therefore -- predefined --

Signed and Sealed this
Tenth Day of October, 2017

Joseph Matal
*Performing the Functions and Duties of the*
*Under Secretary of Commerce for Intellectual Property and*
*Director of the United States Patent and Trademark Office*